United States Patent [19]

Southren et al.

[11] Patent Number: 5,376,534
[45] Date of Patent: Dec. 27, 1994

[54] USE OF DECREASED 3-ALPHA-HYDROXYSTEROID DEHYDROGENASE ACTIVITY IN PERIPHERAL LYMPHOCYTES OR OTHER CELLS OF PATIENTS WITH PRIMARY OPEN ANGLE GLAUCOMA AS A DIAGNOSTIC INDICATOR

[75] Inventors: A. Louis Southren, Monsey; Bernard I. Weinstein, New York; Gary G. Gordon, Monsey, all of N.Y.

[73] Assignee: New York Medical College, Valhalla, N.Y.

[21] Appl. No.: 169,611

[22] Filed: Dec. 17, 1993

[51] Int. Cl.$^5$ .......................... C12Q 1/32; G01N 33/48
[52] U.S. Cl. ............................ 435/26; 435/4; 435/810; 435/975; 436/63; 436/808; 514/912; 514/913
[58] Field of Search ............... 435/26, 4, 810, 975; 436/63, 808; 514/912, 913

[56] References Cited

U.S. PATENT DOCUMENTS 4,863,912 9/1989 Southren et al. ................. 514/93

OTHER PUBLICATIONS

Southren et al, *Chemical Abstracts*, vol. 100, p. 321, Ref. #32937k, 1984 (Invest. Opthalmol. Visual Sci. 1983, 24(10), 1413–17).

*Primary Examiner*—Michael G. Wityshyn
*Assistant Examiner*—Abdel A. Mohamed
*Attorney, Agent, or Firm*—Zarley, McKee, Thomte, Voorhees & Sease

[57] ABSTRACT

An assay for determining patients either having Primary Open Angle Glaucoma or at risk of developing Primary Open Angle Glaucoma. The assay involves testing cells, preferably lymphocyte cells, for 3α-HSD activity and determining from the level of assayed activity whether the patient is either suffering from Primary Open Angle Glaucoma or at risk therefor.

7 Claims, No Drawings

USE OF DECREASED 3-ALPHA-HYDROXYSTEROID DEHYDROGENASE ACTIVITY IN PERIPHERAL LYMPHOCYTES OR OTHER CELLS OF PATIENTS WITH PRIMARY OPEN ANGLE GLAUCOMA AS A DIAGNOSTIC INDICATOR

BACKGROUND OF THE INVENTION

For years people have been attempting to develop a convenient screening assay to determine whether a patient has Primary Open Angle Glaucoma (POAG) or is at risk for developing POAG. The currently used diagnosis is based on an evaluation of a patient's visual field and many risk factors such as intraocular pressure, family history of Glaucoma, race, age, and the appearance of the optic disk. All of these factors are considered in reaching the diagnosis of POAG. However, the testing is not simple, requires a highly skilled person for proper evaluation, and is extremely time-consuming and expensive and is unreliable.

Because of the above-referenced current method of diagnosis of POAG or risk for developing POAG, there is a continuing need and has been a continuing search for a clear marker, or test system, that can be used in mass testing of the public to determine POAG risk. In earlier work of these co-inventors reported in U.S. Pat. No. 4,863,912, and a divisional application which matured into U.S. Pat. No. 4,997,826, these present co-inventors developed a therapy for Tetrahydrocortisol use in Glaucoma treatment.

Tetrahydrocortisol is a normal cortisol metabolite found in urine and serum of normal humans but not in Trabecular Meshwork (TM) cells isolated from POAG eyes. Cortisol is metabolized only slowly by normal TM cells. However, in TM cells from primary open angle glaucoma (POAG) patients, the rate limiting enzyme delta-4-reductase is aberrantly hyperexpressed, and activity of the 3-oxidoreductase (also called 3-hydroxysteroid dehydrogenase) is reduced. This enzyme imbalance leads to the accumulation of 5-alpha and 5-beta-dihydrocortisol in POAG TM cells. It was in these patients that it was postulated that 5-beta-dihydrocortisol is toxic to TM cells and compromises TM function. Since the trabecular meshwork is the major site for aqueous humor outflow, compromised TM function leads to an increase in intraocular pressure. It is believed that tetrahydrocortisol may antagonize the action of 5-beta-dihydrocortisol, in a yet to be defined manner, and that it also may function as an inhibitor of A-ring reductase activity.

In earlier work of these co-inventors reported in 1983 in *Investigative Ophthalmology & Vis Science* (24:1413, 1983) and 1985 in *Investigative Ophthalmology and Vis Science* (26:890, 1985), it was reported that 5-beta-dihydrocortisol is metabolized in the TM cells by an enzyme 3-alpha-hydroxysteroid dehydrogenase (3-alpha-HSD) to 3-alpha, 5-Beta-Tetrahydrocortisol. This is a normal metabolic pathway. In the earlier work as reported, the inventors identified two enzyme defects in cultured trabecular meshwork from patients with Primary Open Angle Glaucoma. As compared to control cells, the POAG derived cells had an increase in cortisol delta 4-reductase and a decrease in 3-alpha-hydroxysteroid dehydrogenase. This finding, however, had little diagnostic value since it required culturing cells from either autopsy eyes or from surgical specimens. Put another way, an assay on cells from the TM is simply not practical as something that can be used on the population at large to determine POAG risk. Therefore, in 1983 in an effort to find a further diagnostic assay, an enzyme which was observed to have a dramatic increase in patients suffering from trabecular meshwork cells, namely cortisol delta-4 reductase, was tested in peripheral lymphocytes from blood samples of patients known to be suffering from Glaucoma as compared to patients known not to be suffering from Glaucoma. The levels of cortisol delta-4 reductase were found to be the same in POAG and non-POAG derived specimens. Therefore, it was then concluded that there was no correlation between levels of this enzyme in the TM and the levels in cells in the blood specimens, and the search for a correlating enzyme as a diagnostic marker stopped.

It can be seen that there is a real and continuing need for a simple, general population test that can be used on the public at large by laboratory workers to determine patient risk of Primary Open Angle Glaucoma.

Thus it is a primary objective of the present invention to provide a mass screening assay which can be used as a marker test for POAG and those patients at risk of developing POAG, which are collectively referred to herein as "at risk" patients.

Another objective of the present invention is to provide such an assay which is simple, straightforward and which can be properly interpreted by people of lower skill levels than those required to make the overall composite evaluations presently used in the medical field that involve such subjective data as evaluation of visual field, family history, race, age and appearance of the optic disk.

Another objective of the present invention is to develop a simple blood assay test which correlates predictably and easily and quickly with Primary Open Angle Glaucoma risk determination.

Yet another objective of the present invention is to develop a simple testing kit which can be used in determining Primary Open Angle Glaucoma risk.

The method and means of accomplishing these objectives as well as others will become apparent from the detailed description of the invention which will follow hereinafter.

SUMMARY OF THE INVENTION

An assay for determining patients at risk of Primary Open Angle Glaucoma is provided. The assay involves obtaining a patient blood sample and testing cells in the blood sample for 3-alpha-hydroxysteroid dehydrogenase enzyme activity to determine if it is significantly decreased from the normal level of patients not suffering from POAG. From the developed data the patient is categorized as either an at risk patient for POAG, a patient that has POAG, or a patient that has no present risk of POAG.

DETAILED DESCRIPTION OF THE INVENTION

As reported in our earlier work of 1983 and 1985, there were two enzyme defects in cultured trabecular meshwork cells observed in patients with Primary Open Angle Glaucoma. However, since the increased levels of the enzyme Cortisol delta 4 reductase found in TM cells did not correlate with blood cells, it was presumed that the second enzyme phenomena observed in TM cells, namely a decrease in 3-alpha-hydroxysteroid dehydrogenase (3-alpha-HSD) would also not correlate.

Surprisingly, however, it has now been found that the decrease in 3-alpha-hydroxysteroid dehydrogenase (3-alpha-HSD) found in TM cells does correlate with a corresponding decrease in 3-alpha-HSD in peripheral lymphocyte cells. This unpredicted and previously unobserved phenomena provides the basis for the current assay.

It is not known why patients suffering from Primary Open Angle Glaucoma or at high risk in developing the same have a decreased activity of 3-alpha-HSD in the trabecular meshwork. Nor is it known why this observed phenomena of enzyme decrease for 3-alpha-HSD correlates with peripheral lymphocyte assays when the earlier observed phenomena of increase of delta-4 reductase does not correlate. However, this unpredicted phenomena does provide the basis for a uniform assay which can be performed quickly and easily on peripheral blood samples of the public at large. Moreover, because differences in level, i.e., decrease in 3-alpha-HSD in patients at risk of Primary Open Angle Glaucoma and those not suffering from POAG is marked (in many instances the normal patients have a twofold or threefold higher level of 3-alpha-HSD in comparison with POAG patients), the test results are extremely easy to interpret.

It should be mentioned that this diagnostic indicator only functions effectively for Primary Open Angle Glaucoma. Patients suffering from Secondary Glaucomas, e.g., Glaucoma caused by physical damage to the eye such as scar tissue, etc., that does not involve a defective functioning of the TM cells and cannot be predicted by this assay. Nevertheless, the assay is extremely useful because most Glaucoma sufferers in fact suffer from Primary Open Angle Glaucoma, as opposed to Secondary Glaucomas.

In accordance with the process of the present invention, lymphocytes are simply isolated from venous blood, and labeled 5-beta-dihydrocortisol (3H-5-beta-DHF) is added. If 3-alpha-HSD is present, it will metabolize the labeled 5-beta-DHF in accordance with the following equation:

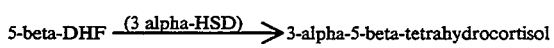

Thus, if lots of 3-alpha-5-beta-tetrahydrocortisol is produced, that is an indicator of high levels of 3-alpha-HSD since it is needed for the reaction to proceed. Correspondingly, if little of the 5-beta-DHF is converted to 3-alpha-5-tetrahydrocortisol, that is evidence of decreased levels 3-alpha-HSD. In other words, the amount of produced tetrahydrocortisol directly corresponds to the level of 3-alpha-HSD. Higher levels of tetrahydrocortisol mean higher levels of 3-alpha-HSD, and correspondingly, lower levels of tetrahydrocortisol mean lower levels of 3-alpha-HSD.

The amount of tetrahydrocortisol produced is quantified and expressed in units of specific activity measurement. Generally speaking, on average the units of activity of 3-alpha-HSD in normal patients are found to be $27.5 \times 10^{-14}$ moles of 3-alpha-5-beta-tetrahydrocortisol formed per hour at 37° C. per 1 million cells as compared to $13.7 \times 10^{-14}$ moles of 3-alpha-5-beta-tetrahydrocortisol formed per hour at 37° C. per 1 million cells in POAG patients. The difference between the two groups was found to be highly significant. As can be seen, a marked difference exists that can easily be observed.

The following examples are offered to illustrate but not limit the process of the present invention.

EXAMPLES

Sixteen (16) patients known to be suffering from Primary Open Angle Glaucoma and sixteen (16) non-POAG patients were selected as controls.

Isolation of peripheral blood lymphocytes:

Blood samples are collected using the anti coagulant EDTA and used within 4 hrs of collection. Two volumes of RPMI medium (Gibco BRL) are added to 1 volume of blood, it is layered on Ficol (Pharmacia) and centrifuged for 20 mins. at 2000 rpm. The lymphocyte layer is removed with a Pasteur pipette and washed three times with the RPMI medium and finally resuspended in the same medium (1–2 million cells per ml). An equal amount of trypan blue is mixed with an aliquot for counting with a hemocytometer.

3α-HSD Assay:

0.05 μCi of $^3$H-5-beta-dihydrocortisol (5-beta-DHF) is added to borosilicate tubes and evaporated to dryness. The labeled 5-beta-DHF is prepared by incubating labeled cortisol with a suitable biological material such as bacteria or mammalian liver or adrenal extract which metabolizes the cortisol to 5-beta-DHF and other products. The 5-beta-DHF formed is isolated and purified by standard methods using High Performance Liquid Chromatography. 0.5 ml of lymphocyte suspension is added to the 5-beta-DHF test tube and incubated at 37° C. for 1 hr. Control tubes are incubated with the medium and substrate. After incubation all of the steroids are extracted with 5 ml of ethylacetate and evaporated to dryness. The labeled steroids are separated on Thin Layer Chromatography and quantitated. The activity is expressed in moles of 3-alpha-5-beta-tetrahydrocortisol (3-alpha-5-beta-THF) formed per hour at 37 ° C. per $1 \times 10^6$ cells.

In the following table, the activities are expressed as $10^{-14}$ moles of 3-alpha-5-beta-THF formed per hour at 37 ° C. per 1 million cells. These are the same units as expressed earlier.

TABLE

| PATIENTS | NORMAL CONTROL | (POAG PATIENTS) |
|---|---|---|
| 1 | 32.0 | 14.0 |
| 2 | 33.0 | 8.0 |
| 3 | 40.0 | 14.0 |
| 4 | 43.0 | 11.0 |
| 5 | 31.0 | 6.0 |
| 6 | 20.0 | 14.0 |
| 7 | 24.0 | 25.0 |
| 8 | 27.0 | 14.0 |
| 9 | 29.0 | 15.0 |
| 10 | 22.0 | 11.0 |
| 11 | 22.0 | 18.5 |
| 12 | 21.0 | 9.0 |
| 13 | 40.0 | 13.5 |
| 14 | 23.0 | 26.6 |
| 15 | 17.0 | 7.5 |
| 16 | 16.7 | 12.6 |
| MEAN: | 27.5 | 13.7 |
| SD: | 8.3 | 5.7 |
| SE: | 2.1 | 1.4 |

$P < 0.0001$

The reduction of 3-alpha-HSD activity for the patients was similar to earlier work previously reported for trabecular meshwork of POAG patients. The reduced levels of 3-alpha-HSD activity in the POAG patients suggests its role in the etiology of POAG, i.e., a deficiency in 3-alpha-HSD activity results in the formation of decreased amounts of the hypotensive metabolic 3-alpha-5-beta-tetrahydrocortisol. Thus it can be seen that this simple blood test can be used to identify patients at risk for Primary Open Angle Glaucoma. As can be seen from the data and earlier description as well, those patients that are at risk of POAG or that in fact have it, generally have 3-alpha-HSD levels of from 25% or more and generally 50% or more lower than the levels of normal patients. Using the units herein expressed, the range is generally from 0 to 24 for at risk patients and preferably or most frequently from 3 to 17 for patients classified as at risk.

It should be mentioned that in addition to enzyme activity measurements in peripheral blood lymphocytes, a similar diagnosis could be predicated upon other cells or an antibody or nucleic acid based assay in lymphocytes or other cells as well. These changes are contemplated as within the spirit and scope of the invention.

The test solutions and instructions therefor can be conveniently provided in a simple assay test kit. It can therefore be seen that the invention accomplishes all of its stated objectives.

What is claimed is:

1. An assay method for determining patients having Primary Open Angle Glaucoma (POAG) or at risk of developing POAG, said method comprising:
    assaying a cell sample of the patient to be tested for 3-alpha-hydroxysteroid dehydrogenase activity; and classifying from the level of assayed activity whether the patient is an at risk patient for POAG.

2. The assay method of claim 1 wherein the cells are of blood sample of peripheral lymphocyte cells.

3. The assay method of claim 1 wherein the patients with units of activity of 3-alpha-hydroxysteroid dehydrogenase within the range of 0 to 24 are classified as POAG risk patients.

4. The assay method of claim 1 wherein the patients with units of activity of 3-alpha-hydroxysteroid dehydrogenase within the range of from 3 to 17 are classified at risk.

5. The assay method of claim 1 wherein those patients having an assay of 3-alpha-hydroxysteroid dehydrogenase as measured by $10^{-14}$ moles of 3-alpha-5-beta-tetrahydrocortisol formed per hour at 37° C. per million cells is within the range of from 0 to 24 for patients classified as POAG at risk.

6. The assay method of claim 5 wherein the 3-alpha-hydroxysteroid dehydrogenase units are within the range of from 3 to 17 for patients classified as at risk.

7. An assay kit for determining patients having risk of Primary Open Angle Glaucoma, said assay kit including, means for withdrawing a blood sample of a patient to be tested for 3-alpha-hydroxysteroid dehydrogenase activity; and
    means for testing activity of 3-alpha-hydroxysteroid dehydrogenase enzyme in a drawn blood sample of a patient; and
    means for determining from the level of assayed activity whether the patient is an at risk patient for Primary Open Angle Glaucoma.

* * * * *